(12) United States Patent
Manuel

(10) Patent No.: US 12,067,379 B2
(45) Date of Patent: Aug. 20, 2024

(54) METHOD FOR PROCESSING A MEDICAL DATA SET BY AN EDGE APPLICATION BASED ON A CLOUD-BASED APPLICATION

(71) Applicant: Siemens Healthcare GmbH, Erlangen (DE)

(72) Inventor: Sujith Manuel, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 207 days.

(21) Appl. No.: 17/324,498

(22) Filed: May 19, 2021

(65) Prior Publication Data
US 2021/0373871 A1    Dec. 2, 2021

(30) Foreign Application Priority Data
May 28, 2020 (DE) .................. 10 2020 206 726.0

(51) Int. Cl.
G06F 8/61      (2018.01)
G16H 40/40     (2018.01)

(52) U.S. Cl.
CPC ............... *G06F 8/63* (2013.01); *G16H 40/40* (2018.01)

(58) Field of Classification Search
CPC .......... G06F 8/61; G06F 8/63; G06F 9/44526; G16H 40/40
See application file for complete search history.

(56) References Cited

U.S. PATENT DOCUMENTS

| | | | |
|---|---|---|---|
| 10,565,349 B2 * | 2/2020 | Shiibashi | H04L 67/62 |
| 2005/0017972 A1 * | 1/2005 | Poole | A61B 8/461 |
| | | | 345/424 |
| 2005/0074157 A1 * | 4/2005 | Thomas, III | G16H 30/20 |
| | | | 705/3 |
| 2009/0067693 A1 * | 3/2009 | Shinagawa | G06T 7/0012 |
| | | | 382/128 |
| 2010/0088117 A1 | 4/2010 | Belden et al. | |
| 2013/0208966 A1 * | 8/2013 | Zhao | G06Q 40/08 |
| | | | 709/219 |

(Continued)

FOREIGN PATENT DOCUMENTS

| | | |
|---|---|---|
| EP | 3451341 A1 | 3/2019 |
| WO | WO-2018015414 A1 * | 1/2018 .......... G06K 9/0014 |

OTHER PUBLICATIONS

German Office Action for German Application No. 10 2020 206 726.0 dated Feb. 9, 2021.

*Primary Examiner* — Marina Lee
(74) *Attorney, Agent, or Firm* — Harness, Dickey & Pierce, P.L.C.

(57) ABSTRACT

A computer-implemented method is for processing a medical data set at a processing system by at least one edge application. In an embodiment, the method includes receiving the medical data set from a medical system, the medical system and the processing system being parts of a local network. The method furthermore includes initializing the at least one edge application based on a cloud-based application, the cloud-based application being stored within a cloud system and the cloud system being separated from the local network. The at least one edge application is a software application executable by the processing system. The method further includes processing the medical data set by the at least one edge application, thereby generating a processed medical data set; and providing the processed medical data set.

21 Claims, 6 Drawing Sheets

(56) References Cited

U.S. PATENT DOCUMENTS

| | | | |
|---|---|---|---|
| 2014/0114672 A1 | 4/2014 | Wright et al. | |
| 2016/0048944 A1* | 2/2016 | Ashmole | A61B 6/032 |
| | | | 382/131 |
| 2016/0239615 A1* | 8/2016 | Dorn | G16H 40/20 |
| 2017/0017907 A1 | 1/2017 | Narasimhan et al. | |
| 2017/0228229 A1* | 8/2017 | Jain | H04L 67/01 |
| 2018/0032675 A1* | 2/2018 | Dominick | G16H 30/20 |
| 2018/0375728 A1* | 12/2018 | Gangil | H04L 41/0853 |
| 2019/0304610 A1* | 10/2019 | Shiibashi | G06F 16/27 |
| 2020/0081426 A1* | 3/2020 | Kane | H04L 67/10 |
| 2020/0218580 A1* | 7/2020 | Kim | G06F 9/5072 |
| 2021/0074415 A1* | 3/2021 | Chen | G16H 40/67 |
| 2021/0134406 A1* | 5/2021 | Manuel | G16H 10/60 |

* cited by examiner

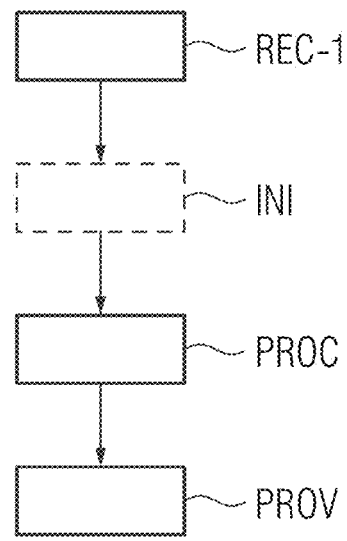
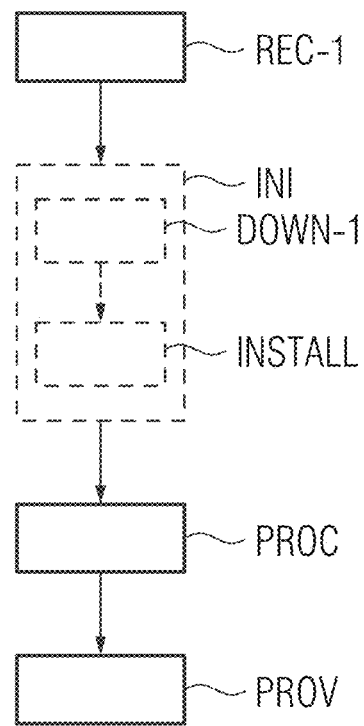

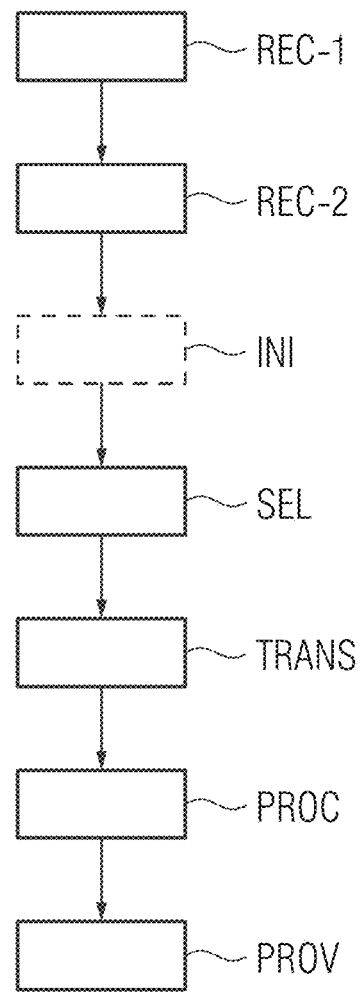

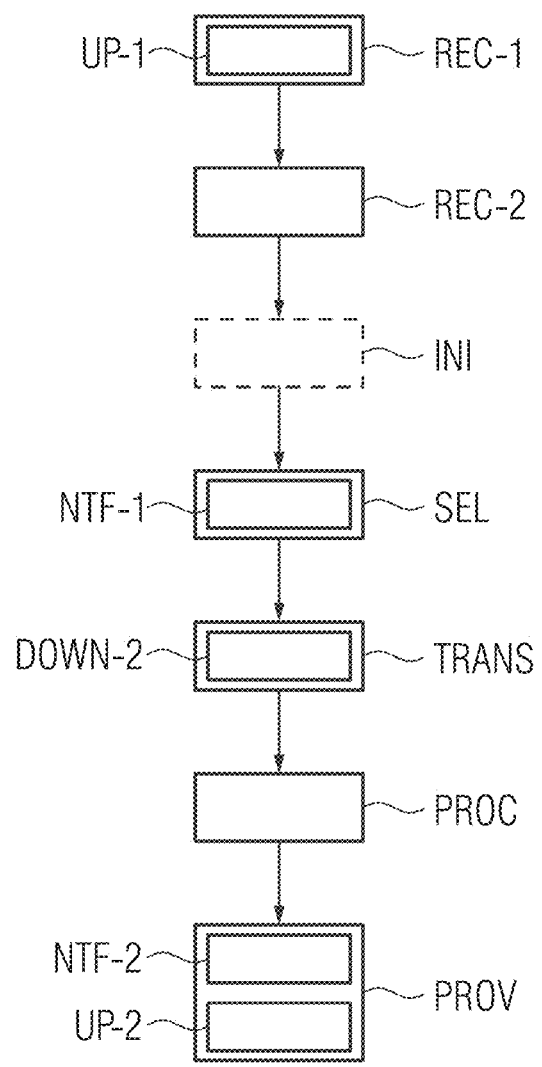

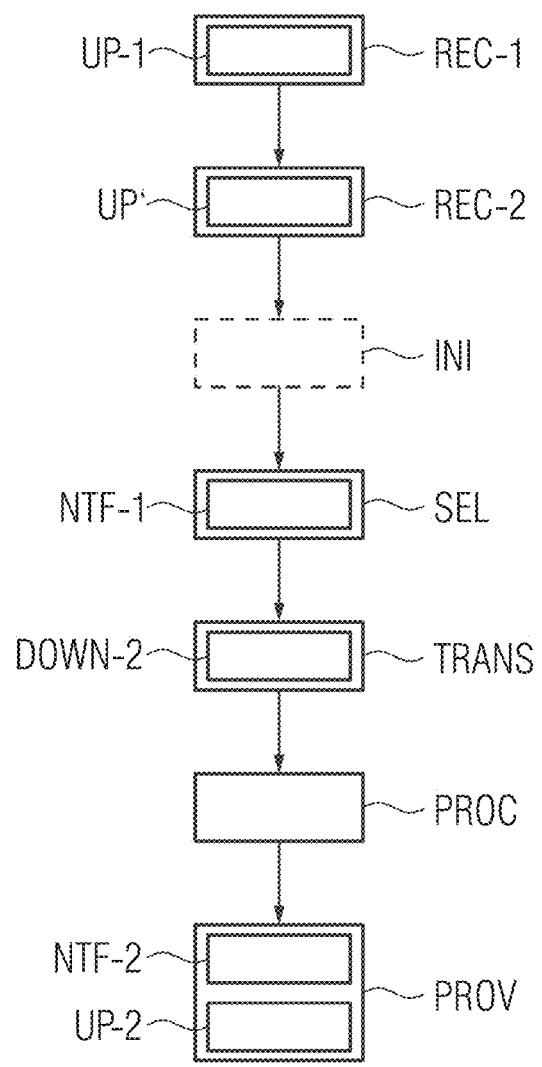

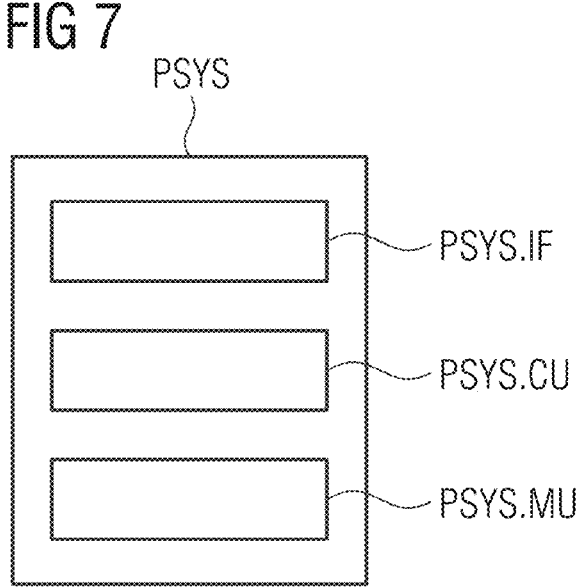

METHOD FOR PROCESSING A MEDICAL DATA SET BY AN EDGE APPLICATION BASED ON A CLOUD-BASED APPLICATION

PRIORITY STATEMENT

The present application hereby claims priority under 35 U.S.C. § 119 to German patent application number DE 102020206726.0 filed May 28, 2020, the entire contents of which are hereby incorporated herein by reference.

FIELD

Example embodiments of the invention generally relate to a method and a device for processing a medical data set at a processing system by at least one edge application, wherein the processing system is part of a local network.

BACKGROUND

Several cloud-based applications are available for different use cases. A cloud-based application can for example be used to process data according to a specific use case. Such data can be acquired by a system which is part of a local network of an institution for example of a hospital or doctor's office. For processing the data with the cloud-based application, it has to be transmitted from the local network to the cloud-based application. Such a cloud-based application is executed in a cloud system, hence the data to be processed has to be transmitted to the cloud system.

Dependent on the size of the data to be processed the process of transmitting takes some time and bandwidth resources, and a stable connection between the local network and the cloud system is necessary.

Furthermore, if transmitting data from the local network to the cloud system, data protection guidelines must be taken into account depending on the kind and the content of the data transmitted to the cloud system. This is particularly important with regard to medical data. The data protection guidelines for transmitting medical data are strict and some data is not allowed to leave the local network.

Hence, in order to reduce processing time of the data and/or to ensure compliance with the data protection guidelines, it is in some cases more convenient to process the data locally at the institution in a processing system of the local network.

Nevertheless, such cloud-based applications are often external, not compatible applications which cannot easily be implemented into the processing system of the local network of an institution.

SUMMARY

At least one embodiment of the present invention provides a method to process a medical data set by an edge application, wherein the edge application is based on a cloud-based application and is executed by the processing system.

Embodiments are directed to a method, a processing system, a computer program product and a computer-readable storage medium according to the independent claims. Advantageous features and further developments are listed in the claims and in the following specification.

In the following, the embodiments according to the invention are described with respect to the processing system as well as with respect to the methods. Features, advantages or alternative embodiments herein can be assigned to the other objects and vice versa. In other words, claims for the processing system can be improved with features described or claimed in the context of the methods. In this case, the functional features of the method are embodied by objective units of the processing system.

In a first embodiment, the invention relates to a computer-implemented method for processing a medical data set at a processing system by at least one edge application. The method comprises the step of first receiving the medical data set from a medical system, wherein the medical system and the processing system are parts of a local network. The method furthermore comprises the step of initializing the at least one edge application based on a cloud based application, wherein the cloud-based application is stored within a cloud system, the cloud system being separated from the local network and wherein the edge application is a software application executed by the processing system. The method furthermore comprises the step of processing the medical data set by the at least one edge application, thereby generating a processed medical data set. The method furthermore comprises the step of providing the processed medical data set. In particular, providing the processed medical data set can comprise storing, transmitting and/or displaying the medical data set.

In a second embodiment, the invention relates to a processing system for processing a medical data set at the processing system by at least one edge application. The processing system comprises an interface and a computation unit. The interface is configured for first receiving the medical data set from a medical system, wherein the medical system and the processing system are parts of a local network. The interface and/or the computation unit is configured for initializing the at least one edge application based on a cloud-based application, wherein the cloud-based application is stored within a cloud system, the cloud system being separated from the local network and wherein the edge application is a software application executed by the processing system. The computation unit is furthermore configured for processing the medical data set by the at least one edge application, thereby the processed medical data set is generated. The interface is furthermore configured for providing the processed medical data set.

In a third embodiment, the invention relates to a computer program product with a computer program and a computer-readable medium. A mainly software-based implementation has the advantage that even previously used processing systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a further embodiment, the invention relates to a computer program product comprising program elements directly loadable into a memory unit of a first providing system, which induces the processing system to execute the method according to the method and its embodiments when the program elements are executed by the processing system.

In a fourth embodiment, the invention relates to a computer-readable storage medium comprising program elements which are readable and executable by a processing system, to execute the claimed method and its embodiments, when the program elements are executed by the processing system.

In at least one embodiment, the invention relates to a computer-implemented method for processing a medical data set at a processing system by at least one edge application, the method comprising:

receiving the medical data set from a medical system, the medical system and the processing system being parts of a local network;

initializing the at least one edge application based on a cloud-based application, the cloud-based application being stored within a cloud system and the cloud system being separated from the local network, wherein the at least one edge application is a software application executable by the processing system;

processing the medical data set by the at least one edge application, to generate a processed medical data set; and providing the processed medical data set.

In at least one embodiment, the invention relates to a processing system for processing a medical data set at the processing system by at least one edge application, the processing system comprising:

an interface, configured to first receive the medical data set from a medical system, the medical system and the processing system being parts of a local network; and at least one processor, at least one of the interface and the at least one processor being configured to initialize the at least one edge application based on a cloud-based application, the cloud-based application being stored within a cloud system and the cloud system being separated from the local network, wherein the at least one edge application is a software application executable by the processing system, wherein at least one processor is further configured to process the medical data set by the at least one edge application, to generate a processed medical data set, and wherein the interface is further configured to provide the processed medical data set.

In at least one embodiment, the invention relates to a non-transitory computer program product storing program elements, directly loadable into a memory of a processing system, to induce the processing system to execute the method of an embodiment when the program elements are executed by the processing system.

In at least one embodiment, the invention relates to a non-transitory computer-readable storage medium storing program elements, readable and executable by a processing system, to execute the method of an embodiment when the program elements are executed by the processing system.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

FIG. 1 displays a schematic flow chart of a first embodiment of the method for processing a medical data set at a processing system by at least one edge application, FIG. 2 displays a schematic flow chart of a second embodiment of the method for processing a medical data set at a processing system by at least one edge application, FIG. 3 displays a schematic flow chart of a third embodiment of the method for processing a medical data set at a processing system by at least one edge application, FIG. 4 displays a schematic flow chart of a fourth embodiment of the method for processing a medical data set at a processing system by at least one edge application, FIG. 5 displays a schematic flow chart of a fifth embodiment of the method for processing a medical data set at a processing system by at least one edge application, FIG. 6 displays a schematic flowchart of an embodiment of the systems and components involved in the method for processing a medical data set at a processing system by at least one edge application, FIG. 7 displays a processing system.

DETAILED DESCRIPTION OF THE EXAMPLE EMBODIMENTS

Figure 6:
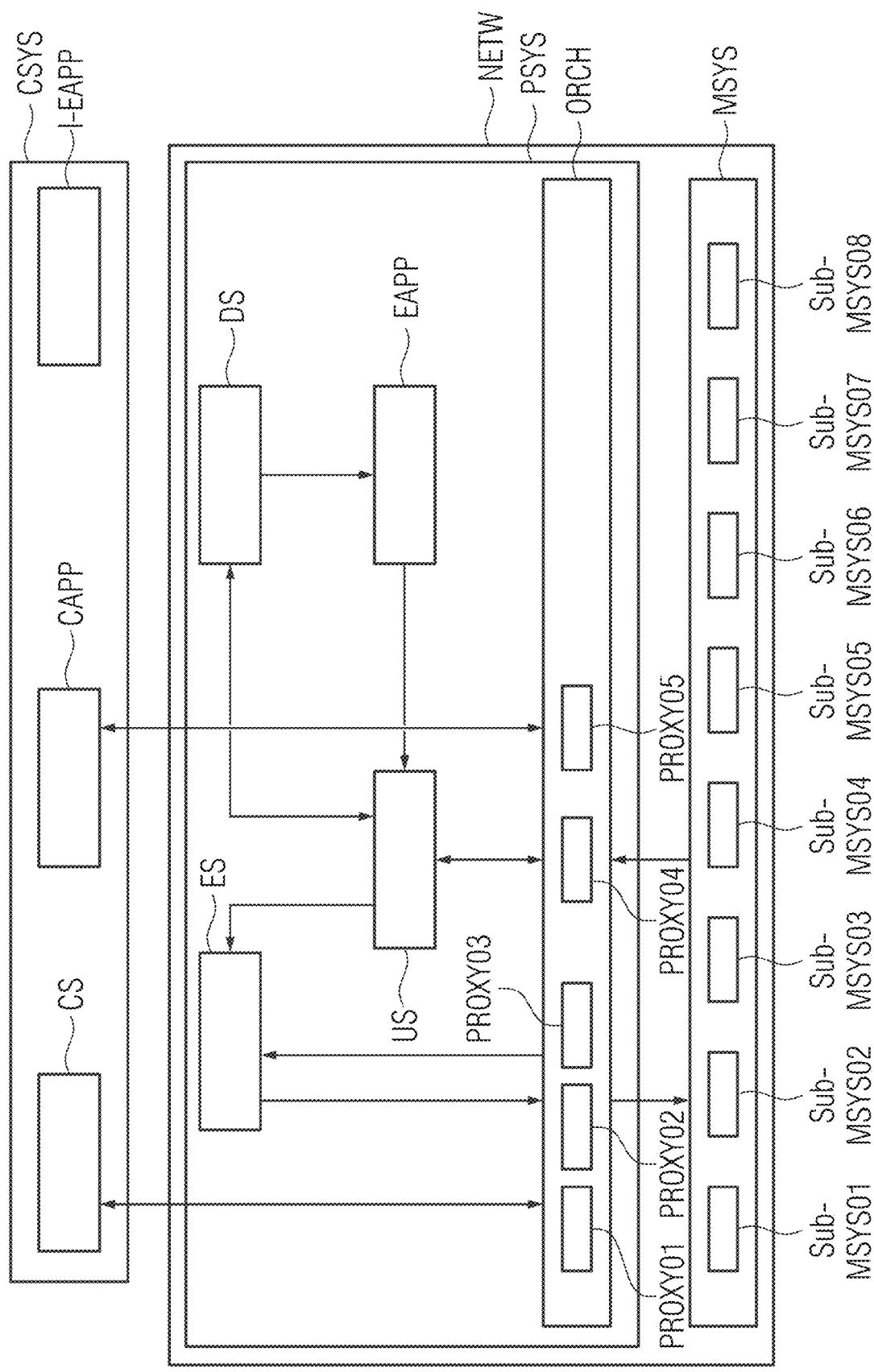

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the invention relates to a computer-implemented method for processing a medical data set at a processing system by at least one edge application. The method comprises the step of first receiving the medical data set from a medical system, wherein the medical system and the processing system are parts of a local network. The method furthermore comprises the step of initializing the at least one edge application based on a cloud based application, wherein the cloud-based application is stored within a cloud system, the cloud system being separated from the local network and wherein the edge application is a software application executed by the processing system. The method furthermore comprises the step of processing the medical data set by the at least one edge application, thereby generating a processed medical data set. The method furthermore comprises the step of providing the processed medical data set. In particular, providing the processed medical data set can comprise storing, transmitting and/or displaying the medical data set.

In particular, the processing system is part or component of the local network. In particular, the local network is located at an institution like for example a hospital or a doctor's office etc., in other words, the local network is formed by data processing software and/or hardware at said institution. In particular, the local network is a self-contained system. In particular, a medical data set leaving the network must be preprocessed in accordance with data protection guidelines, e.g., it must be anonymized or pseudonymized. In particular, the medical data set to be processed at the processing system is not allowed at all to leave the local network of the institution.

In particular, the processing system is separated from the cloud system. In particular, the cloud system is hosted by a server which is not placed at the institution which hosts the processing system. In particular, the processing system and the cloud system are spatially separated. In particular, separated also means that the cloud system has no direct access to data which is stored or processed by the processing system. The cloud system can only access such data with special permission and/or if the data is actively sent to the cloud system, wherein data protection guidelines must be observed. In particular, the cloud system is not part of the self-contained processing system, and vice versa.

The edge application is a software application which is executed by the processing system. In particular, the medical data set which is processed by the edge application is processed at the local network. With other words, processing the medical data set by the edge application implies that the medical data set is processed locally and does not need to leave the institution and/or the local processing system for being processed. The edge application is based on the cloud-based application. In other words, it exists a cloud-based application which can be used to process the medical data set in the same manner as the edge application. The difference between the edge application and the cloud-based application is that the edge application processes the medical data set locally at the processing system and the cloud-based application processes the medical data set in the cloud system. In particular, the edge application as well as the cloud-based application can be an external application. In other words, the edge application and the cloud-based application can originate from another party than the processing system itself.

In particular, the edge application is based on the cloud-based application and the cloud-based application being compiled and/or interpreted based on a common source code. In particular, the source code for the edge application and the source code for the cloud-based application can be identical in more than 50% of their parts, in particular, in more than 75% of their parts, in particular, in more than 90% of their parts, and in particular, they can be identical, in all cases not taking into account external libraries used by the edge application and/or the cloud-based application. In particular, if the edge application and the cloud-based application are compiled software applications, both can be compiled for different processing architectures, with different compiler options or with different compilers. In particular, the edge application and the cloud-based application can be linked against different (shared or static) libraries or can interact with different external systems based on a common API (acronym for "application programming interface").

In the step of first receiving the medical data set, the data to be processed by the edge application is received from the medical system by the processing system. The medical data set, in particular, can comprise an image data and/or an electronic patient record and/or laboratory diagnostic information and/or information about pre-existing illnesses of a patient etc. These are different types of medical data sets. The medical data set can be related to a patient. In particular, it can be acquired during an examination of the patient and/or it can describe medical facts about the patient etc. The medical system can for example comprise an imaging system (e.g. an X-ray device, a computed tomography device, a magnetic resonance device, a positron emission tomography device, a single photon emission computed tomography device etc.) and/or a laboratory diagnostic device and/or a picture archiving and communication system (acronym: PACS) and/or a radiological information system (acronym: RIS) and/or a hospital information system (acronym: HIS). Such systems can be called sub medical systems of the medical system. In other words, the medical system can comprise a device and/or an IT system of the institution. In particular, the medical system can comprise a plurality of different sub medical systems. In particular, the medical system is a part of the local network, similar to the processing system. In particular, data respectively the medical data set within the local network can be transmitted between systems like the medical system and/or the processing system of the local network. In particular, for transferring data respectively medical data set between systems of the local network it is not necessary to pre-process the data respectively medical data set according to the data protection guidelines.

In the step of initializing the at least one edge application, the edge application is initialized at the processing system. In particular, before being initialized at the processing system, the edge application is provided by the cloud system to the processing system. In this step, the edge application is initialized locally at the processing system such that the medical data set can be processed by the edge application locally at the local processing system. Hence, no medical data set has to be transferred to the cloud system to be processed by the edge application. As mentioned above, the edge application is developed respectively built based on an existing cloud-based application. In other words, the edge application is based on the corresponding cloud-based application. In particular, the step of initializing the edge application has to be applied at least once for a single edge application. After initializing the at least one edge application at the processing system, it can be used to process medical data sets. In other words, if the at least one edge application has been initialized previously, the step of initializing may potentially not be needed to be performed again. In other words, the step of initializing the at least one edge application is an optional step. In particular, the step of initializing the at least one edge application can alternatively be executed before executing the step of first receiving the medical data set.

In the step of processing the medical data set, the medical data set is processed by the at least one edge application. In particular, the processing depends on the at least one edge application and on the medical data set which should be processed. Processing the medical data set can for example comprise: pattern recognition and/or image/contrast enhancement and/or masking image data and/or highlighting a suspicious finding and/or clustering techniques and/or applying machine learning algorithms and/or applying artificial intelligence algorithms and/or searching comparable medical data sets in the PACS, RIS or HIS and/or creating an automatic diagnosis etc. In the step of processing the medical data set the processed medical data set is generated. In particular, the processed medical data set is the result after executing the edge application onto the medical data set. The processed medical data set can be of the same type as the medical data set, e.g., if the medical data set is a medical image, the processed medical data set could be a segmented medical image. Alternatively, the processed medical data set can be of another type than the medical data set, e.g., if the medical data set is a medical image, the processed medical data set could be the probability of the presence of a certain structure within the medical image.

In the step of providing the processed medical data set, the processed medical data set is provided. In particular, providing the processed medical data set can comprise storing the processed medical data set. The processed medical data set can in particular be stored in the PACS and/or RIS and/or RIS. In particular, providing the processed medical data set can comprise sending the processed medical data set to the PACS and/or RIS and/or HIS and/or a sub medical system. In particular, the medical data set can be provided to a user. The user can for example be a medical staff and/or the patient. The medical staff can for example be a doctor and/or a nurse etc. The processed medical data set can, in particular, be provided to the user via the PACS and/or the RIS and/or the HIS. In this case, the processed medical data set is loaded respectively downloaded into the PACS and/or RIS and/or HIS in the step of providing the processed medical data set. In particular, the processed medical data set can be provided via the medical system to the user. In particular, the processed medical data set can be provided via a sub medical system to the user. In particular, the sub medical system for providing the processed medical data set can be different from the sub medical system from which the medical data set is received in the step of first receiving the medical data set. In particular, the user can be informed when the processed medical data set is available for example in the PACS and/or RIS and/or HIS. In particular, the user can be informed by an e-mail and/or by a pop-up window etc.

The inventors recognized that it is possible to initialize an edge application at the processing system which is developed in correspondence to respectively based on a cloud-based application. In particular, the inventors recognized that by this method it is possible to process a medical data set locally. This helps to comply with the data protection guidelines. Additionally, this saves time as no data has to be transferred to an external cloud server. Furthermore, it is not necessary to provide a stable connection between the local network and the cloud server. In particular, the inventors recognized that the correspondence between the edge application and the cloud-based application allows a centralized maintenance of the applications. In particular, the medical data set can be processed in the same way by different applications. Hence, the user can choose the most suitable way to process the medical data set: locally at the processing system or in the cloud-system. Especially with regard to medical data, it is important that two processed medical data sets are comparable even if one of the processed medical data sets has been processed in the local processing system an the other one in the cloud-system. This ensures a diagnostic standard von medical data sets.

According to a further embodiment of the invention, the at least one edge application is based on an image of the at least one edge application.

In particular, the edge application is published as an image of the edge application within the cloud system. With other words, the image of the edge application is provided by the cloud system. In particular, the image of the at least one edge application can be published on a cloud repository. In particular, the image of the edge application comprises all information necessary to install and/or execute the edge application on the processing system. In particular, the image of the at least one edge application can be provided via an executable file which can be downloaded from the cloud system. In particular, the image of the edge application can be downloaded from the cloud system. In other words, the edge application can be downloaded from the cloud system. In particular, the edge application can be downloaded to the processing system of the local network. In particular, the image of the edge application can comprise the source code. In particular, in this case the source code has to be compiled at the processing system. Alternatively, the image of the edge application can comprise the bytecode of the edge application. This bytecode can be compiled just in time at the processing system while executing the edge application or it can be interpreted by an interpreter of the processing system. Alternatively, the image of the edge application comprises the compiled machine code which can be directly executed by the processing system after downloading the image.

The inventors recognized that it is the most efficient way to provide the at least one edge application as an image which can be downloaded and installed by the processing system.

According to a further embodiment of the invention, the step of initializing the at least one edge application comprises the steps of first downloading the image of the at least one edge application stored within the cloud system and installing the image of the at least one edge application within the processing system.

In particular, in the step of first downloading the image of the at least one edge application all information which is necessary to install and execute the edge application at the processing system is downloaded. This information is provided via the image of the edge application. In particular, the processing system can download the image of the at least one edge application automatically. In particular, such automatic download can be controlled by a specific license which are stored in the processing system. In particular, the specific license can refer to one specific edge application. The specific license can be checked by the cloud system before downloading the at least one edge application respectively the image of the at least one edge application. In other words, if the specific license according to the at least one edge application is available at the processing system, the image of the at least one edge application can be downloaded automatically. In particular, the specific license can be bought respectively acquired and owned by the user. In other words, the user has to buy or acquire a specific license according to the at least one edge application to get the permission to download the at least one edge application to the processing system. In particular, this specific license has to be bought once for initializing the at least one edge application once at the processing system. In particular, the specific license comprises a file which is stored at the processing system and/or the cloud system. In particular, the specific license can comprise a key which is stored at the processing system and/or the cloud system. In particular, the specific license can be used to check an identity of the processing system. In particular the specific license is maintained in the cloud system and/or in the processing system. In particular, the image of the edge application is stored securely in the cloud system, in particular in a cloud repository of the cloud system. Access of the processing system in order to download the image of the edge application is strictly controlled by checking the specific license of the processing system. After initializing the at least one edge application can be executed several times.

In particular, in the step of installing the image of the at least one edge application, the image of the at least one edge application is configured such that the edge application can be executed at the processing system. If necessary, the image of the edge application can be compiled such that the edge application can be executed at the processing system. In particular, if the image is provided by an executable file, for installing the image of the at least one edge application the executable file is executed. In particular, the edge application can be executed several times for a plurality of medical data after being installed.

The inventors recognized that by providing the edge application via the cloud system, it is easy to initialize the edge application within the processing system. In particular, access to the image of the edge application is provided via the cloud system and no further installation medium like an USB stick or a hard disk etc. is necessary for installing/ initializing the edge application. In particular, the inventors recognized that an update of the edge application can be provided via the cloud system. Furthermore, the inventors recognized that by publishing the image via the cloud system it is possible that a plurality of different processing systems which are part of different local networks have access to the image and can download the image according to a specific license.

According to a further embodiment of the invention, a plurality of edge applications is executable by the processing system. The method furthermore comprises the step of second receiving associated data by the processing system, wherein the associated data is related to the medical data set. The method additionally comprises a step of selecting the at least one edge application from the plurality of edge applications based on the associated information by the processing system. The method further comprises a step of transmitting the medical data set to the at least one edge application.

In particular, the edge applications of the plurality of edge applications are all initialized at the processing system as described above. In particular, each edge application can be specialized to process the medical data set in a specific way. In particular, each edge application can be specialized for a specific type of medical data set.

In the step of second receiving the associated data, the associated data is received by the processing system. The associated data is related to the medical data set which is received in the step of first receiving the medical data set by the processing system. The associated data comprises information how the medical data set should be processed. In particular, the associated data comprises information by which edge application of the plurality of edge applications the medical data set should be processed. In particular, the associated information can comprise more than one edge application which should be applied/executed to process the medical data set. In particular, the associated data comprises a link to the at least one edge application which should be used to process the medical data set. In particular, this link can comprise information how data can be transmitted to the at least one edge application at the processing system. Alternatively, the associated data can comprise the name of the at least one edge application. By a virtual dictionary this name can be linked to the at least one edge application itself. The virtual dictionary can be stored and provided by the processing system. The name can be the whole name, an acronym, an abbreviation, etc. of the at least one edge application. Alternatively, the edge application which should be applied for executing the medical data set can be deduced indirectly from the associated data. For example, the associated data can comprise information by which device the medical data set has been acquired or which body region is imaged in the medical data set etc. This information can be used to deduce the best suited edge application or edge applications for processing the medical data set. In particular, the edge application can be chosen by rule-based-programming.

The associated data can in particular be provided by the medical system respectively by a sub medical system. Alternatively, the associated data can be provided manually by a user input. In particular, the associated data can be part of the medical data set. For example the associated data can be a DICOM (abbreviation for "Digital Imaging an Communications in Medicine") header if the medical data set is a medical image data.

The associated data can be created automatically. In this case, the associated data is for example created based on the type of the medical data set and/or the type of examination the medical data set is acquired from etc. Alternatively or additionally, the associated data can be created and/or manipulated and/or adapted manually. In particular, the associated data can be created, manipulated, and/or adapted by the user. In particular, the associated data can be provided by the medical system.

In particular, the associated data can define more than one edge application for processing the medical data set.

In the step of selecting the at least one edge application is selected according to the associated data. In particular, the information provided by the associated data is read out. This information is used to select the at least one edge application which should be applied/executed for processing the medical data set.

In the step of transmitting the medical data set, the medical data set is transmitted to the edge application which is selected in the previous step of selecting the at least one edge application. According to the associated information, the medical data set can be transmitted to more than one edge application. In particular, as all edge applications are part of the local network, no data protection guidelines have to be taken into account transmitting the medical data set.

The inventors recognized that processing the medical data set can be controlled by the associated information. In particular, the inventors recognized that it is possible to accelerate the workflow by providing and/or processing automatically created associated data. Furthermore, the inventors recognized that it is alternatively or additionally possible to create, adapt and/or manipulate the associated data manually. This enables a user to process the medical data set in a personalized manner in dependence of the patient who the medical data set belongs to or the examination etc.

According to a further embodiment of the invention, the associated information comprises processing information whether the medical data set should be processed with the cloud-based application or with the edge application based on the cloud-based application.

As described above, each edge application is based on a cloud-based application. In particular, the edge application and the corresponding cloud-based application process the medical data set in the same manner, but for processing the medical data set with the cloud-based application the medical data set has to be transmitted to the cloud system. In particular, the orchestrator can control the data transmission based on the processing information of the associated data.

In particular, the processing information provided by the associated data can define whether the medical data set should be processed by the edge application inside the processing system or by the corresponding cloud-based application inside the cloud system.

This processing information can for example be set by the user. The user can decide in dependence of the time and resources available and the medical data set to be processed if the data should be processed locally by the edge application or in the cloud by the cloud-based application. Alternatively or additionally the processing information can be set automatically depend on rules set by the user. Alternatively, these rules can be set by the provider of the processing system.

Alternatively, this processing information can be determined automatically in dependence of the type of the medical data set. If the medical data set comprises for example an electronic patient record, the data might be too sensible to send it to the cloud system. Hence, it might be more convenient to process such data with the edge application. In contrast, if the medical data set comprises a medical image which can easily be anonymized it might be advisable to process this data with the cloud-based application in the cloud system as it is easy to conduct the data protection guidelines.

Alternatively or additionally, the processing information in the associated data can be set in dependence of the size of the medical data set. If the medical data set is large it might take too long to upload the whole medical data set into the cloud system. In this case it might be more convenient to process the data locally by the edge application. If the medical data set is small enough it might be advisable to process the data with the cloud-based application. A threshold for defining which data of which size might be processed by the edge application and which be the corresponding cloud-based application depends for example on a bandwidth of the connection between the processing system and the cloud system. This threshold can be set manually or automatically.

Alternatively or additionally, the processing information can be determined based on results and parameters of a previously processing of other medical data sets. In particular, the said parameter could be the processing time of a previously processing of said other medical data sets. Depending on the processing time of the previously processed medical data sets, the processing information can be determined. It can be determined which type of medical data sets take longer being processed by the cloud-based application and which takes longer being processed by the edge application. This can also be determined in dependence of the size of the medical data set. This determination can be performed by a machine learning algorithm or an artificial intelligence algorithm.

The inventors recognized that in some cases it is more convenient to process the medical data set locally with the at least one edge application and in other cases it is more convenient to process it with the corresponding cloud application. They recognized that a type of switch can be installed by providing the processing information via the associated data to the orchestrator.

According to a further embodiment of the invention, the steps of first receiving the medical data set, second receiving the associated data, selecting the at least one edge application, transmitting the medical data set to the at least one edge application, and providing the processed medical data set are supervised by an orchestrator according to the associated data, wherein the orchestrator is a software application executed by the processing system.

In particular, the orchestrator is a software application which controls the above mentioned steps of first receiving the medical data set, second receiving the associated data, selecting the at least one edge application, transmitting the medical data set to the at least one edge application, and providing the processed medical data set. In particular, the orchestrator is informed when the medical data set is received by the processing system. In particular, the orchestrator is informed when the associated data set is received by the processing system. In particular, the orchestrator is informed about the information comprised by the associated data. In particular, the orchestrator performs selecting the at least one edge application by informing the at least one edge application that there is a medical data set which should be processed by the at least one edge application. With other words, the orchestrator activates the at least one edge application according to the associated information. In particular, this activation of the at least one edge application by the orchestrator leads to a transmission of the medical data set to the at least one edge application and to a processing of the medical data set by the at least one edge application. In particular, the orchestrator is informed when the step of processing the medical data set by the at least one edge application is finished. In particular, the orchestrator can initiate the step of providing the processed medical data set after the step of processing the medical data set is finished. In particular, the orchestrator can supervise how to provide the processed medical data set to the user. In particular, the orchestrator can provide a path where the processed medical data set should be stored for providing it to the user. In particular, the orchestrator can initiate to load the processed medical data set into the PACS and/or RIS and/HIS of the local network.

In particular, the orchestrator comprises at least one proxy. In particular, a proxy, which is comprised by the orchestrator, can be designed as an interface between the medical system and the at least one edge application. In particular, a proxy, which is comprised by the orchestrator, can be designed as an interface between the at least one edge application and a system which is designed to provide the processed medical data set to the user. Such a system can be e.g. the PACS and/or the RIS and/or the HIS etc. In particular, several further proxies can be comprised by the orchestrator. These proxies are designed to connect at least two systems of the local network with each other. Connecting comprises for example at least one of activating, data uploading, data downloading, data exchange, informing etc.

The inventors recognized that the systems of the local network can be connected by a central supervising unit, the orchestrator. The inventors recognized that like this integration of at least one edge application into the local network is more efficient. The inventors recognized that a central supervising unit like the orchestrator helps to keep the overview over the single processes executed by the processing system. In particular, the inventors recognized that this simplifies the maintenance of the processing system.

According to a further possible embodiment of the invention, the orchestrator is designed to communicate with the cloud system.

In particular, the orchestrator comprises a proxy which serves as an interface between the processing system and the cloud system. In particular, this interface for example can be used to download the image of the at least one edge application to the processing system. In particular, this interface can prevent an unallowed data exchange between the cloud system and the processing system. In particular, it can be ensured by this interface that only data that comply with the data protection guidelines can be transmitted to the cloud system.

The inventors recognized that the communication between the cloud system and the processing system can be controlled respectively supervised by the orchestrator. In particular, the inventors recognized that maintenance of the processing system is simpler if also the proxy for communicating with the cloud system is hosted by the orchestrator as this provides a general overview of all interfaces respectively proxies of the processing system.

According to a further embodiment of the invention, the step of selecting the at least one edge application and/or the step of providing the processed medical data comprise the step of notifying the at least one edge application or the orchestrator by an Event Service, wherein the Event Service is a first container plugin being executed by the processing system.

A general description concerning a plugin architecture is provided by the document EP 3 451 341 A1, the entire contents of which are hereby incorporated herein by reference. A container plugin is designed to run an application/software application. The container plugin comprises all necessary packages/software which are necessary to run the application of the plugin. In particular, the application executed by the container plugin is independent of the system which executes the container plugin. In particular, such a container plugin can be wrapped in the form of a "docker image" and can be hosted via the software application "Docker".

In particular, instead of comprising a proxy between the medical system and the at least one edge application, the orchestrator can at least comprise a proxy which serves as an interface between the medical system and the Event Service. In particular, the at least one edge application can directly communicate with the Event Service. In particular, the Event Service can be informed/notified by the orchestrator according to the associated information that the Event Service should activate the at least one edge application. With other words, the Event Service informs the at least one edge application that there is a medical data set which should be processed by the at least one edge application. This is done in the step of notifying the at least one edge application.

In the step of providing the processed medical data set, the Event Service is informed/notified by the at least one edge application that the processed medical data set is available. The Edge Service informs the orchestrator via a further proxy. This is done in the step of notifying the orchestrator After being notified by the Event Service, the orchestrator initializes for example to download the processed medical data set to the PACS and/or RIS and/or HIS etc. of the institution. In particular, the Event Service can provide an information how to download the processed medical data set to the orchestrator. This information can originate from the orchestrator itself, from the associated data and/or from further configuration data of the processing system.

The inventors recognized that for communicating with the Edge Application the orchestrator has to include only two proxies. In particular, it is not necessary that the orchestrator comprises a proxy for each edge application of the plurality of edge applications. The inventors recognized that this simplifies creating, maintaining and hosting the orchestrator. The inventors recognized that the Event Service can be designed such that each edge application of the plurality of edge applications can directly communicate with the Event Service.

According to a further embodiment of the invention, the steps of first receiving the medical data set, and of providing the processed medical data set comprise the step of uploading the medical data set and/or the processed medical data set to an Upload Service. Thereby the Upload Service is a second container plugin executable by the processing system and the Upload Service stores the medical data set end/or the processed medical data set.

In particular, the Upload Service is a container plugin as described above with respect to the Event Service.

In the step of first receiving the medical data set, the orchestrator uploads the medical data set to the Upload Service via a proxy. Alternatively, the orchestrator supervises an upload of the medical data set from the medical system to the Upload Service. The medical data set is stored in the Upload Service. In the step of providing the processed medical data set, the processed medical data set is uploaded from the at least one edge application to the Upload Service. Hence, the orchestrator has to comprise no proxy for a direct communication between the medical system and the edge application. The orchestrator has to comprise at least one proxy for communicating with the Upload Service. The processed medical data set can be downloaded from the Upload Service to any local system like the PACS and/or RIS and/or HIS etc. This is supervised by the orchestrator. In particular, the Event Service can provide an information how and/or where to download the processed medical data set from the Upload Service to the orchestrator.

The inventors recognized that the medical data set and the processed medical data set can be stored by the Upload Service, which is a second contained plugin. This allows a centralized data management. Furthermore, the inventors recognized that the orchestrator does not need a proxy for each edge application. Instead it is sufficient if the orchestrator comprises at least a proxy for communicating with the Upload Service.

According to a further embodiment of the invention, the step of transmitting the medical data set to the at least one edge application comprises the step of downloading the medical data set data set stored in the Upload Service via a Download Service by the at least one edge application. Thereby the Download Service is a third container plugin executed by the processing system.

In particular, the Download Service is a container plugin as described above with respect to the Event Service.

In particular, data stored in the Upload Service is provided to the at least one edge application via the Download Service. The at least one edge application is activated respectively informed respectively notified by the Event Service that there is a medical data set in the Upload Service which should be processed by the at least one edge application. This medical data set can be accessed by the at least one edge application via the Download Service. Hence, the Download Service has an interface with the at least one edge application and the Upload Service that is designed to transmit the medical data set from the Upload Service to the at least one edge application.

The inventors recognized that providing the medical data set to the at least one edge application can be controlled by another container plugin the so-called Download Service. In particular, this simplifies the maintenance of the whole processing system.

According to a further embodiment of the invention, a configuration of the processing system and/or the image of the at least one edge application is stored within the cloud system, in particular, in a Configuration Service within the cloud system.

In particular, the configuration of the processing system can comprise details about the local network. In particular, such details can comprise information about systems in the local network and/or about the orchestrator of the processing system and/or about data protection guidelines concerning the medical data set processed in the local network, etc. In particular, the configuration can comprise information about the specific license respectively specific licenses which are stored in the processing system and/or the cloud system respectively owned by the user of the processing system. In particular, the configuration can comprise at least one parameter which can be defined for the at least one edge application. With other words, the parameter can describe how to process the medical data set with the at least one edge application and/or it can refine the processing of the medical data set by the at least one edge application. In particular, the configuration can comprise information on how the processed medical data set should be downloaded for providing the processed medical data set. In particular, the configuration can comprise auto routing rules which are defined for DICOM image data, if the medical data set and/or the processed medical data set is a DICOM image data. In particular, operational aspects of the processing system can be comprised by the configuration. In particular, the configuration can comprise information about by which edge application a specific type of medical data set should be processed. In particular, the configuration can comprise rules which edge application should be used to process the medical data set in dependence of the type of the medical data set or the device the medical data set has be acquired with etc.

In particular, an image of each application of the plurality of edge applications which is initialized at the processing system can be stored by the Configuration Service. In particular, in case of a system crash of the processing system, the edge applications can be re-initialized at the processing system again without interaction with the cloud system. In particular, the edge application can be re-initialized without providing again the specific license.

In particular, data defining the processing system can be stored in the Configuration Service. In particular, all data which must not be protected due to data protection guidelines can be stored in the Configuration Service.

In particular, the orchestrator can communicate with the Configuration Service. In particular, the orchestrator can communicate with the Configuration Service via a proxy respectively via an interface.

In particular, a plurality of Configuration Services can be executed by the cloud system. Thereby each Configuration Service can communicate with an orchestrator of a different processing system of a different local network.

The inventors recognized that storing at least a configuration of the processing system within the Configuration Service helps to re-install and/or re-initialize the processing system after a crash. In particular, the inventors recognized that it is helpful to store configuration data in an independent system like the cloud system.

According to a further embodiment of the invention, the at least one edge application is downloadable from the cloud system. Thereby the Configuration Service provides updates of the at least one edge application.

In particular, the Configuration Service is informed when an update of the at least one respectively of one edge application of the plurality of edge applications which are initialized at the processing system is provided by the cloud system. In particular, the Configuration Service initializes a download of the update to the processing system where the update can be installed. Alternatively, the update is provided to the Configuration Service. In this case, the update is sent directly by the Configuration Service to the processing system.

In particular, all the communication, data exchange etc. between the processing system and the Configuration Service is supervised by the orchestrator.

The inventors recognized that the Configuration Service can serve as an instance of the cloud system which provides useful information from the cloud system to the processing system. In particular, the inventors recognized that the Configuration Service can choose such updates for the edge applications that are initialized at the processing system. In other words, the inventors recognized that the Configuration Service can serve as filter, which filters such information of the cloud system which is of interest for the processing system.

According to a further embodiment of the invention, a backup of the processing system and/or the at least one edge application is stored in the Configuration Service.

In other words, an image of the whole processing system can be stored in the Configuration Service of the cloud system. In particular, the backup can be an image of the processing system. In case of a crash of the processing system in the local network, the image can be downloaded to the local network. After installing the image of the processing system, it is the same as before the crash.

Alternatively or additionally, an image of the at least one edge application can be stored in the Configuration System. If just the at least one edge application of the processing system crashes, it can be re-initialized by downloading it from the Configuration Service. In particular, this image of the at least one edge application can comprise user-specific parameter settings which are defined for the specific processing system. These settings can be defined by the user of the processing system.

The inventors recognized that for maintenance of the processing system, it is helpful to have a backup of the system in an independent system like the cloud system. The inventors recognized that this image normally does not comprise patient specific data which has to be protected by data protection guidelines. The inventors recognized that in the case that the image comprises data which has to be protected by data protection guidelines such data can be anonymized or pseudonymized. The inventors recognized that it is helpful to store the images of the initialized edge applications into the Configuration Service. These images can be personalized as parameter settings can be added to these images. The inventors recognized that this simplifies a re-setup of the processing system after a crash.

According to a further embodiment of the invention, the medical data set comprises medical image data wherein processing the medical data set comprises, in particular, pattern recognition and/or image registration and/or image enhancement and/or masking.

In particular, the medical image data can be acquired for example with an X-ray device, a computed tomography device, a magnetic resonance device, positron emission tomography device, a single photon emission computed tomography device, etc. In particular, such a medical image data can depict a body region of a patient. In particular, such medical image data can be provided according to the DICOM (abbreviation for "Digital Imaging an Communications in Medicine") standard.

In particular, processing the medical image data can comprise pattern recognition. In pattern recognition suspicious structures within the medical image data are detected. Such suspicious structures can for example be tumor structures or anomalies, etc. In particular, pattern recognition helps to find suspicious structures in the medical image data. In particular, pattern recognition can be performed by trained algorithms like deep learning or machine learning or artificial intelligence etc. Alternatively, pattern recognition can be performed by untrained algorithms.

Alternatively or additionally, processing the medical image data can comprise image registration. In particular during image registration two medical image data which mainly depict the same body region can be registered such that both medical image data match as well as possible. In other words, the medical image data can be superposed by the image registration such that a depicted body region superposes as well as possible.

Alternatively or additionally, processing the medical image data can comprise image enhancement. In particular image enhancement can comprise reduction of artifacts and/or sharpening contours and/or enhancing contrast etc. In particular, image enhancement can comprise methods for improving image quality. In particular, details and/or structures in the medical image data which might be important for the user can be enhanced by image enhancement.

Alternatively or additionally, processing the medical image data can comprise masking the medical image data. In particular structures which are not important for the user can be masked while processing. Such masking can be performed by a trained algorithm. Alternatively, masking can be performed by an untrained algorithm like by thresholding and/or edge detection, etc.

In particular, these possibilities to process the medical data set can be provided by one edge application. Alternatively these possibilities can be provided by a combination of more than one edge application.

The inventors recognized that in particular medical image data can be processed by the above described methods. The inventors recognized that cloud-based applications are available for processing medical image data. They recognized that it is helpful to integrate edge applications which are based on such cloud-applications in the local processing system for processing medical image data. In particular, they recognized that it can be avoided to let medical image data leave the local network by processing it with the edge applications.

In a second embodiment, the invention relates to a processing system for processing a medical data set at the processing system by at least one edge application. The processing system comprises an interface and a computation unit. The interface is configured for first receiving the medical data set from a medical system, wherein the medical system and the processing system are parts of a local network. The interface and/or the computation unit is configured for initializing the at least one edge application based on a cloud-based application, wherein the cloud-based application is stored within a cloud system, the cloud system being separated from the local network and wherein the edge application is a software application executed by the processing system. The computation unit is furthermore configured for processing the medical data set by the at least one edge application, thereby the processed medical data set is generated. The interface is furthermore configured for providing the processed medical data set.

In particular, the processing system can be configured to execute the previously described method for processing the medical data set at the processing system by the at least one edge application. The processing system is configured to execute this method and its aspects by the interface and the computation unit being configured to execute the corresponding method steps. In particular, the interface can comprise one or more sub-interfaces. In particular, the computation unit can comprise one or more computation sub-units.

According to a further embodiment of the invention, the processing system comprises an Event Service as a first container plugin, an Upload Service as a second container plugin and/or a Download Service as a third container plugin.

In a third embodiment, the invention relates to a computer program product with a computer program and a computer-readable medium. A mainly software-based implementation has the advantage that even previously used processing systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a further embodiment, the invention relates to a computer program product comprising program elements directly loadable into a memory unit of a first providing system, which induces the processing system to execute the method according to the method and its embodiments when the program elements are executed by the processing system.

In a fourth embodiment, the invention relates to a computer-readable storage medium comprising program elements which are readable and executable by a processing system, to execute the claimed method and its embodiments, when the program elements are executed by the processing system.

FIG. 1 displays a schematic flow chart of a first embodiment of the method for processing a medical data set at a processing system PSYS by at least one edge application EAPP.

The first step of this embodiment is the step of first receiving REC-1 a medical data set from a medical system MSYS by a processing system PSYS. Within the first embodiment, the medical data set comprises medical image data of a patient. Alternatively or additionally, the medical data set can comprise an electronic patient record and/or a laboratory diagnostic information and/or an information about pre-existing illnesses of a patient, etc. In general, the medical data set can comprise data of a patient. In particular, the medical data set can comprise data of the patient which has been acquired during an examination of the patient. Alternatively or additionally, the medical data set can comprise general information about the patient or information about previous illnesses. Within the first embodiment, the medical system MSYS comprises an imaging system (e.g. an X-ray device, a computed tomography device, a magnetic resonance device, a positron emission tomography device, a single photon emission computed tomography device etc.). Alternatively or additionally, the medical system can comprise a laboratory diagnostic device, a picture archiving and communication system (acronym: PACS), a radiological information system (acronym: RIS), and/or a hospital information system (acronym: HIS). In particular, the medical system MSYS can comprise a plurality of different sub medical systems Sub-MSYS01, Sub-MSYS02, Sub-MSYS03, Sub-MSYS04, Sub-MSYS05, Sub-MSYS06, Sub-MSYS07, Sub-MSYS08. In particular, each sub medical system Sub-MSYS01, . . . , Sub-MSYS08 can be one of the above listed systems. In particular, one of the sub medical systems Sub-MSYS01, . . . , Sub-MSYS08 provides the medical data set to the processing system PSYS. The medical system MSYS and the processing system PSYS are part of a local network NETW.

The step of initializing INI the at least one cloud application is not necessarily executed for every medical data set received, but in this embodiment, the step of initializing INI is executed if the at least one edge application EAPP is not yet available at the processing system PSYS. In other words, the step of initializing INI the at least one edge application EAPP is an optional step. In an alternative embodiment, the step of initializing INI the at least one edge application EAPP can be executed before executing the step of first receiving REC-1 the medical data set. The at least one edge application is designed for processing PROC the medical data set. In particular, the at least one edge application EAPP is a software application which is executed by the processing system PSYS. In particular, the at least one edge application EAPP can be an external, not compatible application. That means, that the at least one edge application EAPP is provided by a different party than the processing system PSYS itself. The at least one edge application EAPP is based on a cloud-based application CAPP. This means, that the at least one edge application EAPP and the corresponding cloud-based application CAPP process the medical data set in the same way. Thereby, the at least one edge application EAPP is executed at the processing system PSYS. Instead, the corresponding cloud-based application CAPP is executed by a cloud system CSYS. The cloud system CSYS and the processing system PSYS are separated from each other. This means, that data transfer between these two systems is only possible with specific approval. Such an approval is for example given for initializing the at least one edge application EAPP from the cloud system CSYS. Furthermore, separated can also mean that a server which is used to host the processing system PSYS is located spatially separated from a server which is used to host the cloud system CSYS. In the step of initializing INI the at least one edge application EAPP, the at least one edge application EAPP is initialized at the processing system PSYS such that it can be executed to process the medical data set.

In the next step of processing PROC the medical data set, the medical data set is processed by the edge application EAPP. Thereby, a processed medical data set is generated. In other words, the processed medical data set is the result of processing PROC the medical data set with the at least one edge application EAPP. How the medical data set is processed depends on the one hand on the at least one edge application EAPP which is executed to process the medical data set. On the other hand, how the medical data set is processed depends on a type of the medical data set. Within this first embodiment, the type of the medical data set is image data. Alternatively or additionally, a type of a medical data set can be text data, structured data like DICOM, data of an electronic patient record, etc. In the case that the medical data set comprises medical image data, processing PROC the medical data set can comprise e.g. pattern recognition and/or image enhancement and/or image registration and/or masking, etc. In the case that the medical data set comprises text data, processing PROC the medical data set can e.g. comprise ontology and/or text recognition, etc.

In the step of providing PROV the processed medical data set is provided to a user. The user can for example be a doctor and/or a nurse and/or any other medical staff and/or even the patient himself. In particular, providing PROV the medical data set can be done via the medical system MSYS. In particular, the processed medical data set can be provided via a sub medical system Sub-MSYS01, . . . , Sub-MSYS08 to the user. The sub medical system Sub-MSYS01, . . . , Sub-MSYS08 for providing PROV the processed medical data set to the user can be different or the same as the sub medical system Sub-MSYS01, . . . , Sub-MSYS08 from which the medical data set is received in the step of first receiving REC-1 the medical data set.

FIG. 2 displays a schematic flow chart of a second embodiment of the method for processing a medical data set at a processing system PSYS by at least one edge application EAPP.

The steps of first receiving REC-1 the medical data set, of processing PROC the medical data set and of providing PROV the processed medical data set are executed as described according to FIG. 1, and can comprise all advantageous features described therein.

In this embodiment the optional step of initializing INI the at least one edge application comprises two steps.

The first step comprises first downloading DOWN-1 an image I-EAPP of the at least one edge application EAPP from the cloud system CSYS to the processing system PSYS. The image I-EAPP of the at least one edge application EAPP can for example be an executable (".exe") file which can be executed at the processing system. In particular, the at least one edge application EAPP is built within the cloud system CSYS. The image I-EAPP is published within the cloud system CSYS. If a specific license according to the at least one edge application EAPP is provided by the processing system PSYS, the image ImEdgeSys can be downloaded from the cloud system CSYS to the processing system PSYS. By providing the image I-EAPP via the cloud system CSYS, it is possible to download the image I-EAPP by a plurality of different processing systems PSYS which are part of a plurality of different local networks NETW. If each local network NETW belongs to another institution like a clinic a doctors's office etc. a plurality of institutions has access to the image I-EAPP. This is much easier than publishing the image I-EAPP via a storage medium like a hard disk, a USB drive etc.

In the second step of installing INSTALL the image I-EAPP of the at least one edge application EAPP on the processing system PSYS, the at least one edge application EAPP is installed such it can be executed by the processing system PSYS and it can be used to process the medical data set. In particular, the image I-EAPP is compiled such that the edge application is executable at the processing system. If the image I-EAPP is provided as an executable file, the file is executed.

FIG. 3 displays a schematic flow chart of a third embodiment of the method for processing a medical data set at a processing system PSYS by at least one edge application EAPP.

The steps of first receiving REC-1 the medical data set, of initializing INI the at least one edge application, of processing PROC the medical data set and of providing PROV the processed medical data set are executed as described according to FIG. 1. In an alternative embodiment, the step of initializing INI the at least one edge application can comprise the two steps of first downloading DOWN-1 the image I-EAPP of the at least one edge application EAPP and of installing INSTALL the image I-EAPP according to FIG. 2.

In particular, a plurality of edge applications EAPP can be executable by the processing system PSYS. In particular, the number of executable edge applications EAPP depends on the specific licenses which are provided by the local network NETW respectively the processing system PSYS and which serve as a permission to download the corresponding edge application EAPP from the cloud system CSYS.

In the step of second receiving REC-2 an associated data is received by the processing system PSYS. In an alternative embodiment the step of second receiving REC-2 the associated data can be executed before the step of first receiving REC-1 the medical data set. The associated data comprises information by which edge application EAPP of the plurality of edge applications EAPP the medical data set should be processed. The associated data can also be provided by the medical system MSYS respectively by a sub medical system Sub-MSYS01, . . . , Sub-MSYS08. Alternatively, the associated data can be provided manually by a user input. In an alternative embodiment, the associated data can furthermore comprise processing information. This processing information determines whether the medical data set should be processed by the at least one edge application EAPP as described above and which is defined by the associated data, or if it should be processed in the cloud system CSYS by the corresponding cloud-based application CAPP. The processing information can be determined manually by the user. Alternatively, the processing information can be determined based on the type of the medical data set or the size of the medical data set. If the medical data set comprises sensible data it is more advantageous to process this medical data set locally with the at least one edge application EAPP and not to load it into the cloud system CSYS. If the medical data set is large it might take too long to load it into the cloud system CSYS and it is also preferable to process it locally. A threshold concerning this aspect can either be set manually or automatically in dependence of a bandwidth of the connection between the processing system PSYS and the cloud system CSYS.

The at least one edge application EAPP, which should be used to process the medical data set, is selected in the step of selecting SEL the at least one edge application EAPP according to the associated data.

According to this selection the medical data set is transmitted to the at least one edge application EAPP in the step of transmitting TRANS the medical data set.

The steps of first receiving REC-1 the medical data set, second receiving REC-2 the associated information, selecting SEL the at least one edge application EAPP according to the associated information, transmitting TRANS the medical data set to the at least one edge application EAPP, and providing PROV the processed medical data set are supervised by an orchestrator ORCH. The orchestrator ORCH is designed to control these steps and processes. In particular, the orchestrator ORCH comprises at least one proxy which is necessary to enable the communication and/or data exchange between the single components of the processing system PSYS and between the processing system PSYS and the cloud system CSYS. Possible components of the processing system are schematically depicted and explained in FIG. 6.

FIG. 4 displays a schematic flow chart of a fourth embodiment of the method for processing a medical data set at a processing system PSYS by at least one edge application EAPP.

The steps of first receiving REC-1 the medical data set, of initializing INI the at least one edge application, of processing PROC the medical data set and of providing PROV the processed medical data set are in general executed as described according to FIG. 1. In an alternative embodiment, the step of initializing INI the at least one edge application can comprise the two steps of first downloading DOWN-1 the image I-EAPP of the at least one edge application EAPP and of installing INSTALL the image I-EAPP according to FIG. 2. The steps of second receiving REC-2 the associated data, of selecting SEL the at least one edge application EAPP and of transmitting TRANS the medical data set to the at least one edge application EAPP are in general executed as described according to FIG. 3.

The steps of selecting SEL the at least one edge application EAPP and of providing PROV the processed medical data set comprise a step of notifying NTF-1, NTF-2 the at least one edge application EAPP or the orchestrator ORCH according to the associated data by an Event Service ES. The Event Service ES is a container plugin. It is designed to communicate with the orchestrator ORCH via a proxy PROXY01, PROXY02, PROXY03, PROXY04, PROXY05 of the orchestrator ORCH. Furthermore, the Event Service ES is designed to communicate with the at least one edge application EAPP. In an advantageous embodiment, the Event Service ES is designed to communicate with all edge applications EAPP of the plurality of edge applications EAPP which can be executed by the processing system PSYS.

In the step of selecting SEL the at least one edge application EAPP the Event Service ES is informed by the orchestrator ORCH which edge application EAPP should be used to process the medical data set according to the associated data. Alternatively, the associated data is transferred to the Event Service ES by the orchestrator ORCH and the Event Service ES reads out from the associated data which edge application EAPP should be executed. According to the associated data the Event Service ES notifies respectively informs respectively activates the at least one edge application EAPP. In other words, the Event Service ES informs the at least one edge application EAPP that there is a medical data set available which should be processed. Informing the at least one edge application EAPP is given in the step of notifying NTF-1 the at least one edge application.

In the step of providing PROV the processed medical data set, the Event Service ES notifies the orchestrator ORCH that the processed medical data set is available within the step of notifying NTF-2 the orchestrator ORCH. Hence, the orchestrator ORCH can initiate for example a download of the processed medical data set to the medical system MSYS respectively to a sub medical system Sub-MSYS01, . . . , Sub-MSYS08. For this, the Event Service ES is informed by the at least one edge application EAPP or by an Upload Service US which is described in the following, that the processed medical data set is available.

Like this, it is not necessary, that the orchestrator ORCH is designed to communicate with all edge applications EAPP. As the edge applications EAPP might be external, not compatible applications several different interfaces respectively proxies PROXY01, . . . , PROXY05 might be necessary to communicate with all edge applications EAPP.

In this embodiment, the step of first receiving REC-1 the medical data set and of providing PROV the processed medical data set comprise a step of uploading UP-1, UP-2 the medical data set respectively the processed medical data set to the Upload Service US. The Upload Service US is a second container plugin which is executed by the processing system PSYS. The Upload Service US is designed to store the medical data set and/or the processed medical data set.

In the step of first receiving REC-1 the medical data set, the medical data set is uploaded from the medical system MSYS to the Upload Service US via the orchestrator ORCH in the step of uploading UP-1 the medical data set. Hence, the orchestrator ORCH comprises proxies Prox01, . . . , Prox05 to communicate and/or exchange data between with the medical system MSYS and with the Upload Service US. In an alternative embodiment, the orchestrator ORCH only supervises the transmission of the medical data set from the medical system MSYS to the Upload Service US. The medical data set is stored in the Upload Service US.

In the step of providing PROV the processed medical data set is transmitted from the at least one edge application EAPP to the Upload Service US in the step of uploading UP-2 the processed medical data set. The processed medical set is stored in the Upload Service US. The Upload Service US can inform the Event Service ES that the processed medical data set is available. The Event Service ES then notifies the orchestrator ORCH that the processed medical data set is available. The steps of notifying NTF-2 the orchestrator ORCH by the Event Service ES and of uploading UP-2 the processed medical data set comprised by the step of providing PROV the processed medical data set can be executed in any sequence.

In this embodiment, the step of transmitting TRANS the medical data set to the at least one edge application EAPP comprises the step of second downloading DOWN-2 the medical data set stored in the Upload Service US via a Download Service DS. The Download Service DS is a third container plugin being executed by the processing system PSYS. In other words, the Download Service DS transmits the medical data set to be processed to the at least one edge application EAPP. The at least one edge application EAPP has been notified by the Event Service ES that there is a medical data set available which should be processed by the at least one edge application.

FIG. 5 displays a schematic flow chart of a fifth embodiment of the method for processing a medical data set at a processing system PSYS by at least one edge application EAPP.

The steps of first receiving REC-1 the medical data set, of initializing INI the at least one edge application, of processing PROC the medical data set and of providing PROV the processed medical data set are in general executed as described according to FIG. 1. In an alternative embodiment, the step of initializing INI the at least one edge application can comprise the two steps of first downloading DOWN-1 the image I-EAPP of the at least one edge application EAPP and of installing INSTALL the image I-EAPP according to FIG. 2. The steps of second receiving REC-2 the associated data, of selecting SEL the at least one edge application EAPP and of transmitting TRANS the medical data set to the at least one edge application EAPP are in general executed as described according to FIG. 3.

The steps of notifying NTF-1, NTF-2 the at least one edge application EAPP and/or the orchestrator ORCH by the Event Service ES, of uploading UP-1, UP-2 the medical data set and/or the processed medical data set to the Upload Service US and of second downloading DOWN-2 the medical data set via the Download Service DS are executed according to the description of FIG. 4.

In this embodiment the step of second receiving REC-2 also comprises the step of uploading UP' the associated data to the Upload Service US. The step of uploading UP' the associated data is executed in the same way as the step of uploading UP the medical data set and/or the processed medical data set. In this embodiment, the associated data is also stored in the Upload Service US. This is especially important if the associated information comprises further information about how to process the medical data set. Such information might be important for the at least one edge application EAPP. In this case it is advantageous to upload the associated data to the Upload Serve US such that the at least one edge application EAPP can access the associated data via the Download Service DS. In this embodiment, the Download Service DS is also designed to download the associated data from the Upload Service US to the at least one edge application EAPP.

FIG. 6 displays a schematic drawing of an embodiment of the systems and components involved in the method for processing a medical data set at a processing system PSYS by at least one edge application EAPP.

The local network NETW comprises the medical system MSYS and the processing system PSYS.

The medical system MSYS comprises a plurality of sub medical system Sub-MSYS01, . . . , Sub-MSYS08. Such sub medical systems Sub-MSYS01, . . . , Sub-MSYS08 can be for example an imaging system, a PACS, a RIS, a HIS, a personal computer within the local network etc. The number of sub medical systems Sub-MSYS01, . . . , Sub-MSYS08 is not fixed. In a preferred embodiment, the medical system MSYS comprises at least one sub medical system Sub-MSYS01, . . . , Sub-MSYS08.

The processing system PSYS comprises an orchestrator ORCH, at least one edge application EAPP, an Event Service ES, an Upload Service US and a Download Service DS. Thereby the orchestrator ORCH comprises a plurality of proxies Prox01, . . . , Prox05. The number of proxies is not fixed. The orchestrator ORCH serves as communication interface and as supervisor. The communication structure and/or data exchange structure is visualized by arrows between the systems and components. The orchestrator ORCH can communicate and exchange data with the medical system MSYS. It can furthermore communicate and/or exchange data with the Event Service ES and the Upload Service US, which are part of the processing system PSYS. It can furthermore communicate and/or exchange data with the cloud system CSYS.

The cloud system CSYS comprises a Configuration Service CS, at least one cloud-based application CAPP which corresponds to the at least one edge application EAPP and at least the image I-EAPP of the at least one edge application EAPP.

The Configuration Service CS is designed to store configuration data of the processing system PSYS and/or the at least one edge application EAPP. It can be furthermore designed to provide updates for the at least one edge application EAPP, wherein the update is published within the cloud system CSYS. In some embodiments, the Configuration Service CS is furthermore designed to store a backup respectively an image of the processing system PSYS. This backup can furthermore comprise the initialized edge applications EAPP of the processing system PSYS. It can furthermore comprise a parameters setting of the at least one edge application EAPP. In case of a crash, the whole processing system PSYS can be re-installed including the corresponding edge applications EAPP without providing again a specific license, first downloading DOWN-1 and installing INSTALL the edge applications EAPP.

The cloud-based application CAPP can also be executed for processing the medical data set. For this purpose, the medical data set has to be transmitted into the cloud system CSYS. This can be done via the orchestrator ORCH as indicated by the arrow. For this purpose, the orchestrator ORCH has to be informed that the medical data set should be processed by the cloud-based application CAPP. This can be either done by manual input of a user or this information can be provided by the associated data as processing information. The processing information can be determined manually by the user or automatically based on details according to the medical data set and the connection between the cloud system CSYS and the processing system PSYS.

The image I-EAPP of the at least one edge application EAPP can be downloaded for initializing INI the at least one edge application EAPP at the processing system PSYS.

The interaction between the orchestrator ORCH, the at least one edge application EAPP, the Event Service ES, the Upload Service US, and the Download Service DS is indicated by the arrow. Further explanations concerning these interactions are given in the descriptions according to FIGS. 4 and 5.

For a detailed description of the single steps please refer to FIGS. 1 to 5.

FIG. 7 displays a processing system PSYS. The displayed processing system PSYS is configured to execute a method according to the invention for processing a medical data set by at least one edge application. The processing system PSYS comprises an interface PSYS.IF, a computation unit PSYS.CU, and a memory unit PSYS.MU.

The processing system PSYS can in particular be a computer, a microcontroller or an integrated circuit. Alternatively, the processing system PSYS can be a real or a virtual network of computers (a technical term for a real network is "cluster", a technical term for a virtual network is "cloud"). The processing system PSYS can also be designed as virtual system that is executed on a computer, a real network of computers or a virtual network of computers (a technical term is "virtualization").

An interface PSYS.IF can be a hardware or software interface (for example PCI bus, USB or Firewire). A computation unit PSYS.CU can have hardware elements or software elements, for example a microprocessor or a so-called FPGA (acronym for "field programmable gate way"). A memory unit PSYS.MU can be implemented as a non-permanent working memory (random access memory, RAM for short) or as a permanent mass storage device (hard disk, USB stick, SD card, solid state disk).

The interface PSYS.IF can in particular comprise a plurality of sub-interfaces which carry out different steps of the respective method. In other words, the interface PSYS.IF can also be understood as a plurality of interfaces PSYS.IF.

The computation unit PSYS.CU can in particular comprise a plurality of sub-computing units which carry out different steps of the respective method. In other words, the computation unit PSYS.CU can also be understood as a plurality of computation units PSYS.CU.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for processing a medical data set, the method comprising:
   receiving the medical data set from a medical system, the medical system being part of a local network;
   accessing a cloud system that includes an image of at least one edge application, the at least one edge application corresponding to a cloud-based application stored in the cloud system;
   downloading and installing the image of the at least one edge application from the cloud system on a processing system of the local network to initialize the at least one edge application on the processing system of the local network, wherein the cloud system is separate from the local network, the at least one edge application and the cloud-based application are configured to process the medical data set to produce a same output data set, and the at least one edge application is a software application executable by the processing system;

determining whether to process the medical data set by the at least one edge application or the cloud-based application;

processing the medical data set by at least one of the at least one edge application or the cloud-based application by inputting the medical data set into the at least one edge application or the cloud-based application and generating an output data set, the processing including performing at least one of pattern recognition, image registration, image enhancement or masking on the medical data set; and providing the output data set.

2. The method of claim 1, wherein the at least one edge application includes a plurality of edge applications, executable by the processing system, the method further comprising:

receiving associated data by the processing system, the associated data being related to the medical data set;

selecting the at least one edge application from the plurality of edge applications, based on the associated data received by the processing system; and transmitting the medical data set to the at least one edge application.

3. The method of claim 2, wherein the associated data includes processing information indicating a processing location for the medical data set, the processing location being at least one of the cloud-based application or the at least one edge application.

4. The method of claim 3, wherein the receiving of the medical data set and the providing comprise:

uploading at least one of the medical data set or the output data set to an Upload Service, the Upload Service being a second container plugin executable by the processing system and the Upload Service storing at least one of the medical data set or the output data set.

5. The method of claim 4, wherein the transmitting comprises:

downloading the medical data set stored in the Upload Service via a Download Service by the at least one edge application, wherein the Download Service is a third container plugin being executable by the processing system.

6. The method of claim 2, wherein the receiving of the medical data set, the receiving of the associated data, the selecting, the transmitting, and the providing are supervised by an orchestrator according to the associated data, the orchestrator being a software application executed by the processing system.

7. The method of claim 6, wherein at least one of the selecting of the at least one edge application or the providing of the output data set comprise:

notifying at least one of the at least one edge application or the orchestrator by an Event Service, the Event Service being a first container plugin executable by the processing system.

8. The method of claim 3, wherein the receiving of the medical data set, the receiving of the associated data, the selecting, the transmitting, and the providing are supervised by an orchestrator according to the associated data, the orchestrator being a software application executed by the processing system.

9. The method of claim 1, wherein a configuration of the processing system is stored within a Configuration Service within the cloud system.

10. The method of claim 9, wherein the at least one edge application is downloadable from the cloud system and wherein the Configuration Service provides updates of the at least one edge application.

11. The method of claim 9, wherein a backup of at least one of the processing system or the at least one edge application is stored in the Configuration Service.

12. A non-transitory computer-readable storage medium storing program elements, readable and executable by a processing system, to execute the method of claim 1 when the program elements are executed by the processing system.

13. The method of claim 1, wherein a configuration of at least one of the processing system or the image of the at least one edge application is stored within a Configuration Service within the cloud system.

14. The method of claim 13, wherein the at least one edge application is downloadable from the cloud system and wherein the Configuration Service provides updates of the at least one edge application.

15. The method of claim 13, wherein a backup of at least one of the processing system or the at least one edge application is stored in the Configuration Service.

16. The method of claim 1, wherein a configuration of the processing system is stored within the cloud system.

17. The method of claim 1, wherein the medical data set comprises medical image data.

18. The method of claim 1, wherein the output data set is at least one of a modified version of the medical data set or a different type than the medical data set.

19. The method of claim 1, wherein the output data set includes probabilities of structures within medical images of the medical data set.

20. A processing system for processing a medical data set, the processing system comprising:

an interface, configured to first receive the medical data set from a medical system, the medical system being part of a local network; and at least one processor, at least one of the interface or the at least one processor being configured to access a cloud system that includes an image of at least one edge application, the at least one edge application corresponding to a cloud-based application stored in the cloud system, download and install the image of the at least one edge application from the cloud system on a processing system of the local network to initialize the at least one edge application on the processing system of the local network, wherein the cloud system is separate from the local network, the at least one edge application and the cloud-based application are configured to process the medical data set to produce a same output data set, and the at least one edge application is a software application executable by the processing system, wherein the at least one processor is configured to process the medical data set via at least one of the at least one edge application or the cloud-based application by inputting the medical data set into the at least one edge application or the cloud-based application and generating an output data set, the processing including performing at least one of pattern recognition, image registration, image enhancement or masking on the medical data set, and wherein the interface is configured to provide the output data set.

21. The processing system of claim 20, wherein the processing system includes at least one of an Event Service as a first container plugin, an Upload Service as a second container plugin, or a Download Service as a third container plugin.

* * * * *